United States Patent
Barton et al.

(10) Patent No.: US 12,043,858 B2
(45) Date of Patent: Jul. 23, 2024

(54) $CO_2$ SEQUESTRATION AND CREATION OF CALCIUM CARBONATES THROUGH MICROBIAL INDUCED CARBONATE PRECIPITATION

(71) Applicants: Hazel A. Barton, Akron, OH (US); Matthew Jennings, Akron, OH (US); George Breley, Akron, OH (US)

(72) Inventors: Hazel A. Barton, Akron, OH (US); Matthew Jennings, Akron, OH (US); George Breley, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 260 days.

(21) Appl. No.: 17/306,189

(22) Filed: May 3, 2021

(65) Prior Publication Data
US 2022/0002758 A1    Jan. 6, 2022

Related U.S. Application Data

(60) Provisional application No. 63/047,460, filed on Jul. 2, 2020.

(51) Int. Cl.
*C12P 3/00* (2006.01)
(52) U.S. Cl.
CPC ........................... *C12P 3/00* (2013.01)
(58) Field of Classification Search
CPC ........................................... C12P 3/00
See application file for complete search history.

(56) References Cited

PUBLICATIONS

Han P-P. et al., CN 108220380 A—"Using Two Microorganisms Are Mineralized Process for Preparing Calcium Carbonate", Machine English translation, USPTO (total pp. 1-9), published on Jun. 29, 2018. (Year: 2018).*
Fujisawa M. et al., "Characterization of Bacillus subtilis YfkE (ChaA): a calcium-specific Ca2+/H+ antiporter of the CaCA family", Arch. Microbiol., vol. 191, pp. 649-657. (Year: 2009).*
Dhami N.K. et al., "Biomineralization of Calcium Carbonate Polymorphs by the Bacterial Strains Isolated from Calcareous Sites", J. Microbiol. Biotechnol., vol. 23, No. 5, pp. 707-714. (Year: 2013).*
Ohyama T. et al. "Physiological Role of the chaA Gene in Sodium and Calcium Circulations at a High pH in *Escherichia coli*", J. Bacteriol., Jul. 1994, vol. 176, No. 14, pp. 4311-4315. (Year: 1994).*

* cited by examiner

*Primary Examiner* — Satyendra K Singh
(74) *Attorney, Agent, or Firm* — RENNER KENNER GREIVE BOBAK TAYLOR & WEBER

(57) ABSTRACT

A method for sequestering $CO_2$ and creating precipitated calcium carbonates includes: (a) providing a liquid calcification medium including: a nutrient broth including water and a yeast extract, a carbon source selected from calcium carboxylic acids and calcium dicarboxylic acids and mixtures thereof, and bacteria that naturally express the chaA gene; (b) introducing $CO_2$ to the liquid calcification medium; and (c) allowing microbial induced carbonate precipitation of calcium carbonate, thereby sequestering at least some of the $CO_2$ introduced in the step of introducing.

11 Claims, No Drawings

$CO_2$ SEQUESTRATION AND CREATION OF CALCIUM CARBONATES THROUGH MICROBIAL INDUCED CARBONATE PRECIPITATION

STATEMENT REGARDING FEDERALLY SPONSORED RESEARCH OR DEVELOPMENT

This invention was made with government support under HR0011-18-9-0007 awarded by Defense Advanced Research Projects Agency (DARPA). The government has certain rights in the invention.

FIELD OF THE INVENTION

The present invention relates to $CO_2$ sequestration and the creation of calcium carbonates through microbial induced carbonate precipitation.

BACKGROUND OF THE INVENTION

The most recent report by the Intergovernmental Panel on Climate Change (IPCC) states there is compelling evidence that the accumulation of anthropogenic greenhouse gases ($CO_2$, $CH_4$ and $N_2O$) in the atmosphere has led to an increase in global temperatures over land of 1.53° C., compared to the period from 1850-1900, with half of these emissions occurring since 1980. This warming has contributed to the retreat of glaciers, sea-ice loss, and a global mean sea level rise observed since the 1970s. Other impacts are expected to include increased extreme weather events, reduced food production, reduced biodiversity, ocean acidification, and damage to critical ecosystem services. As a result, climate change represents an existential threat to human society.

There are numerous sources of global $CO_2$ emissions; however, anthropogenic greenhouse gas emissions have been driven largely by economic and population growth. The atmospheric concentrations of carbon dioxide are unprecedented and are at the highest levels they have been in the last 800,000 years. As a result, urgent action is needed to stop and reverse the negative impacts of climate change on ecosystems and society.

The IPCC states that between 1750 and 2011, the cumulative anthropogenic $CO_2$ emissions were 2040±310 $GtCO_2$, about 40% of which have remained in the atmosphere (880±35 $GtCO_2$). While mitigating climate change can be done through policy and behavioral changes, which reduce annual global emissions, it does not remove the current excess $CO_2$ in the atmosphere. To remove this excess requires $CO_2$ sequestration.

Current $CO_2$ sequestration (known as carbon capture and sequestration; CCS) uses three primary approaches: 1) sequestration as biomass through photosynthesis; 2) sequestration as thermodynamically stable mineral carbonates generated using high pressure and high purity $CO_2$ gases; and 3) burial. There are benefits from using photosynthesis, including simplicity (planting trees), and converting $CO_2$ captured as biomass into biofuels and other industrially relevant organic compounds. Nonetheless, there are significant drawbacks to the scale of these projects. CCS using burial requires high quality (>99% pure $CO_2$), high temperatures (>60° C.), and high pressures (up to 150 bar), where the $CO_2$ is injected into either the subsurface or waste alkaline minerals to produce carbonates. Burial is preferred due to simplicity and cost, although there are many drawbacks, including the potential for $CO_2$ escape and inefficient $CO_2$ conversion to stable carbonates.

Microbial metabolic activity can change the chemistry of microenvironments surrounding a cell, leading to altered physiochemical conditions that promote biomineralization. Microbial induced mineralization of $CaCO_3$ is one of the most studied mechanisms of biomineralization. The production of CaCO3 minerals can allow for long-term storage of $CO_2$, as indicated by the ~39 million Gt of $CO_2$ currently preserved in carbonate rocks primarily from the Carboniferous period. The past metabolic activities that have been shown to drive microbial $CaCO_3$ production include photosynthesis, ureolysis, denitrification, ammonification, sulfate reduction, and methane oxidation. Photosynthesis represents the most dominant natural mechanism for calcite biomineralization in the environment, while to date, only ureolysis has been leveraged for CCS. In ureolytic $CaCO_3$ production, bacteria catalyze the breakdown of urea to ammonium and bicarbonate ions. This chemistry increases the amount of ammonium, a weak base, and increases the local pH, driving the precipitation of carbonate ions. Ureolysis has a number of drawbacks, including malodor issues (from the production of ammonia), the limited distribution of naturally occurring ureolytic species, and the viability of ureolysis under extreme conditions.

The present invention provides new methods for sequestration of $CO_2$ and creation of precipitated calcium carbonates through a microbially induced carbonate precipitation.

SUMMARY OF THE INVENTION

An embodiment of the present invention provides a method for sequestering $CO_2$ and creating precipitated calcium carbonates, the method comprising the steps of: (a) providing a liquid calcification medium including: a nutrient broth including water and yeast extract, a carbon source selected from calcium carboxylic acids and calcium dicarboxylic acids and mixtures thereof, and bacteria that naturally express the chaA gene; (b) introducing $CO_2$ to the liquid calcification medium; and (c) allowing microbial induced carbonate precipitation of calcium carbonate, thereby sequestering at least some of the $CO_2$ introduced in said step of introducing.

Another embodiment of the present invention provides a method for sequestering $CO_2$ and creating precipitated calcium carbonates as in any embodiment above, wherein the liquid calcification medium includes from 1 g to 10 g of the yeast extract per 1 L of water; and from 1 g to 50 g of the carbon source per 1 L of water.

Another embodiment of the present invention provides a method for sequestering $CO_2$ and creating precipitated calcium carbonates as in any embodiment above, wherein the liquid calcification medium includes from 2 g/L to 7.5 g/L yeast extract, and from 2.5 g/L to 30 g/L of the carbon source.

Another embodiment of the present invention provides a method for sequestering $CO_2$ and creating precipitated calcium carbonates as in any embodiment above, wherein the carbon source is a metabolizable carbon source.

Another embodiment of the present invention provides a method for sequestering $CO_2$ and creating precipitated calcium carbonates as in any embodiment above, wherein the carbon source is selected from calcium formate, calcium acetate, calcium propionate, calcium butyrate, calcium succinate, and calcium citrate.

Another embodiment of the present invention provides a method for sequestering $CO_2$ and creating precipitated calcium carbonates as in any embodiment above, wherein the carbon source is calcium succinate.

Another embodiment of the present invention provides a method for sequestering $CO_2$ and creating precipitated calcium carbonates as in any embodiment above, wherein the nutrient broth is devoid of urea.

Another embodiment of the present invention provides a method for sequestering $CO_2$ and creating precipitated calcium carbonates as in any embodiment above, wherein the nutrient broth is devoid of acidifying carbohydrate sources that drive one or more of: metabolic overflow, acetogenesis, and mixed acid fermentation.

Another embodiment of the present invention provides a method for sequestering $CO_2$ and creating precipitated calcium carbonates as in any embodiment above, wherein the bacteria are selected from the genera *Bacillus*, *Microbacterium*, and *Escherichia*.

Another embodiment of the present invention provides a method for sequestering $CO_2$ and creating precipitated calcium carbonates as in any embodiment above, wherein the bacteria are selected from *Eschericia coli*, *Escherichia coli* K12, *Bacillus* sp., and *Microbacterium* sp.

Another embodiment of the present invention provides a method for sequestering $CO_2$ and creating precipitated calcium carbonates as in any embodiment above, wherein said step of providing a liquid calcification medium comprises the steps of adjusting the nutrient broth to a pH of from pH 6 or more to pH 9 or less and sterilizing the nutrient broth, both prior to providing the bacteria.

Another embodiment of the present invention provides a method for sequestering $CO_2$ and creating precipitated calcium carbonates as in any embodiment above, after the step of sterilizing the nutrient broth, the step of providing a liquid calcification medium comprises the steps of cooling the nutrient broth to room temperature and adding the carbon source, both prior to providing the bacteria.

Another embodiment of the present invention provides a method for sequestering $CO_2$ and creating precipitated calcium carbonates as in any embodiment above, wherein adding the carbon source includes suspending the carbon source in water to form a suspended carbon source and filter-sterilizing the suspended carbon source.

Another embodiment of the present invention provides a method for sequestering $CO_2$ and creating precipitated calcium carbonates as in any embodiment above, wherein said step of introducing $CO_2$ includes agitating the liquid calcification medium to expose it to $CO_2$ within the surrounding atmosphere.

Another embodiment of the present invention provides a method for sequestering $CO_2$ and creating precipitated calcium carbonates as in any embodiment above, wherein said step of introducing carbon dioxide includes bubbling $CO_2$ through the liquid calcification medium.

Another embodiment of the present invention provides a method for sequestering $CO_2$ and creating precipitated calcium carbonates as in any embodiment above, wherein said step of allowing precipitation of calcium carbonate includes maintaining the liquid calcification medium at a temperature providing aeration for growth of the bacteria.

Another embodiment of the present invention provides a method for sequestering $CO_2$ and creating precipitated calcium carbonates as in any embodiment above, temperature of the liquid calcification medium is maintained at from 10° C. or more to 42° C. or less.

Another embodiment of the present invention provides a method for sequestering $CO_2$ and creating precipitated calcium carbonates as in any embodiment above, wherein the bacteria have a carbonic anhydrase gene, yadF, and the method further comprises the step of engineering yadF into an inducible, overexpression plasmid vector under control of a propionate inducible promotor.

DETAILED DESCRIPTION OF ILLUSTRATIVE EMBODIMENTS

The present invention provides methods for $CO_2$ sequestration and creation of precipitated calcium carbonates, promoting calcification through a previously unexplored microorganism capability previously described in Banks, E. D., Taylor, N. M., Gulley, J., Lubbers, B. R., Giarrizo, J. G., Bullen, H. A., Hoehler, T. M. and Barton, H. A. 2010. Bacterial Calcium Carbonate Precipitation in Cave Environments: A Function of Calcium Homeostasis. Geomicrobiology Journal 27(5): 444-454. Functionally, this approach is similar to published work in calcification and pore closing in the subsurface to seal $CO_2$ reservoirs using bacterial ureolysis (e.g., WO2010075503); however, it is mechanistically different. The present method relies on the toxic nature of intracellular $Ca^{2+}$ ions in bacteria to promote precipitation to remove excess $Ca^{2+}$ by bicarbonate ions sourced from atmospheric $CO_2$, as demonstrated through stable isotope probing. $CO_2$ fixation is promoted by manipulating cell physiology using calcium carboxylate salts as a source of energy. In some embodiments, the process in enhanced by over-expression of the carbonic anhydrase enzyme. $CO_2$ is thus sequestered, being fixed in precipitated calcium carbonates. Through different process conditions and/or ingredient selection, the precipitated calcium carbonates can be of nanometer and micron-scale. These small-scale carbonates, termed precipitated calcium carbonates (PCC) are recoverable from the bacterial-liquid cultures (suspensions) used in the $CO_2$ fixation process and can have a number of industrial uses.

In some embodiments, the present invention provides a method for sequestering $CO_2$ and creating precipitated calcium carbonates, the method including providing a liquid calcification medium; introducing $CO_2$ to the liquid calcification medium; and allowing microbial induced carbonate precipitation (MICP) of calcium carbonate, thereby sequestering at least some of the $CO_2$ and creating a precipitated calcium carbonate for collection and use. The liquid calcification medium is formulated to achieve the desired MICP and includes (a) a nutrient broth including water and a yeast extract, (b) a carbon source selected from calcium carboxylic acids and calcium dicarboxylic acids and mixtures thereof, and (c) bacteria that naturally express the chaA gene.

In some embodiments, the liquid calcification medium includes a yeast extract. In some embodiments, the liquid calcification medium includes 1 g or more of a yeast extract per 1 L of water; and 1 g or more of the carbon source per 1 L of water. In some embodiments, the liquid calcification medium includes from 1 g/L to 10 g/L yeast extract, and from 1 g/L to 50 g/L of the carbon source; in other embodiments, from 2 g/L to 7.5 g/L yeast extract, and from 2.5 g/L to 30 g/L of the carbon source; and, in other embodiments, from 3 g/L to 5 g/L yeast extract, and from 5 g/L to 10 g/L of the carbon source. In one embodiment, the liquid calcification medium includes 4 g/L yeast extract and 7.5 g/L of the carbon source.

In some embodiments, the carbon source used is calcium salt (wherein the salt refers to the ionic assembly of the $Ca^{2+}$ cation with a carboxylic or dicarboxylic anion), allowing the calcium to be taken up with the carbon source by the bacteria for growth. This metabolic pathway uses the uptake of the $Ca^{2+}$ cation by the bacterial cell to cause precipitation and cannot be initiated by simply increasing $Ca^{2+}$ concentrations in the surrounding media. For example, this process does not occur if the media containing a carbon source is simply amended with $CaCl_2$.

In some embodiments, the carbon source is selected from calcium formate, calcium acetate, calcium propionate, calcium butyrate, calcium succinate, and calcium citrate, and mixtures thereof. In some embodiments, the carbon source is calcium succinate. As can be appreciated by a skilled artisan, a liquid culture of the invention can be created by adding exogenous microbes to a liquid culture where growth is initiated by the presence of a calcium carboxylate or dicarboxylic salt, which serves as a carbon source. The carboxylic acid salts that promote $CaCO_3$ precipitation include calcium formate, calcium acetate, calcium propionate, and calcium butyrate. The dicarboxylic acid salts are calcium succinate and calcium citrate.

In some embodiments, the carbon source is added in one or more batch runs, with the carbon being added at 1-10 g/L or added continuously to the culture, to maintain the levels of carbon source at the same rate.

The present MICP process is not urea-dependent and thus can be carried out in a nutrient broth devoid of urea.

The methods of this invention mineralize atmospheric $CO_2$ into $CaCO_3$ by bacterial activity including calcium stress induced by growth on calcium carboxylic and dicarboxylic acid salts. Calcium is an important co-factor in a number of bacterial enzymes; however, the ability of $Ca^{2+}$ to displace other critical divalent metal cations ($Fe^{2+}$, $Mg^{2+}$, etc), requires cellular $Ca^{2+}$ levels to be tightly regulated by the $Ca^{2+/H+}$ anti-porter protein, chaA. Nonetheless, once extracellular $Ca^{2+}$ ion concentrations exceed the thermodynamic export capacity of chaA, $Ca^{2+}$ may leak back into the cell, reaching potentially toxic levels. In order to overcome this, the cell mediates a precipitation reaction by using the carbonic anhydrase (yadF) gene to fix atmospheric $CO_2$ as $HCO_3^-$ (12, 37), increasing extracellular pH. Not only does this pH rise initiate calcification, but it also pulls $Ca^{2+}$ ions out of solution that might otherwise overcome the thermodynamic limits of chaA. This is confirmed by knocking out chaA using site-directed mutagenesis, which demonstrates the loss of the calcification phenotype, while cells grow poorly in the presence of $CaCO_3$. Cellular $Ca^{2+}$ homeostasis is therefore critical to growth in the presence of excess $Ca^{2+}$. This is confirmed by knocking-out the yadF gene, which was found lethal to bacterial growth in the presence of $Ca^{2+}$, while stable isotope probing using $C^{13}O_2$ demonstrated that the source of the carbonates in MICP was atmospheric $CO_2$.

Previous work has examined $CaCO_3$ precipitation on B4 media that has been solidified using 1.4% agar. This media contains 2.5 g/L of calcium acetate (as the $Ca^{2+}$ ion source), 5.0 g/L of glucose (otherwise known as dextrose) and 4.0 g/L of yeast extract, which serves as a source of amino acids and other trace nutrients to enhance microbial growth. Growth in the presence of glucose leads cells to produce carboxylic and other organic acids, produced through a combination of glucose metabolic overflow, acetogenesis, and mixed acid fermentation. As $CaCO_3$ precipitation is related to the pH and saturation index, the presence of glucose leads to the acidification of the media, which reduces the pH and prevents $CaCO_3$ precipitation, which occurs when the pH of the media exceeds the pKa of $HCO_3^- \rightarrow CO_3^{2-}$ due to the presence of these organic acids.

Thus, in some embodiments, the nutrient broth is devoid of acidifying carbohydrate sources that drive one or more of glucose metabolic overflow, acetogenesis, and mixed acid fermentation that would create organic acids and increase acidification. In some embodiments, the nutrient broth is devoid of acidifying carbohydrate sources that would lower pH below 8.2. The removal of these carbohydrates removes the metabolic by-products that would otherwise acidify the media, reducing the likelihood of reaching the $pK_a$ of $HCO_3^-/CO_3^{2-}$ and limiting the precipitation of PCCs.

In some embodiments, the bacteria that naturally express the chaA gene are selected from one or more of the genera *Bacillus, Microbacterium*, and *Escherichia*. In some embodiments, the bacteria are *Bacillus* sp. In some embodiments, bacteria are *Microbacterium* sp. In some embodiments, the bacteria are *Escherichia* sp., and in yet other embodiments, *Escherichia coli* K12.

In order to initiate growth, a colony of the bacterial species is inoculated into a small (<25 mL) culture of standard nutrient broth that contains 5.0 g/L of a pancreatic digest of gelatin and 3.0 g/L of beef extract. This broth is incubated at 20-37° C. with shaking at 200 rpm for 16-24 hours. This starter culture is then inoculated into the calcification media at 1:1,000-10,000 dilution.

In some embodiments, the liquid calcification medium is formed by adding the carbon source to the nutrient broth, and thereafter inoculating with the bacteria. In some embodiments, the liquid calcification medium is formed by sterilizing the nutrient broth before adding the carbon source to the nutrient broth, and thereafter inoculating with the bacteria. In some embodiments, the liquid calcification medium is formed by sterilizing the nutrient broth and adjusting its pH to from pH 6 or more to pH 9 or less before adding the carbon source to the nutrient broth, and thereafter inoculating with the bacteria. In some embodiments, the liquid calcification medium is formed by sterilizing the nutrient broth before adding the carbon source to the nutrient broth, cooling the nutrient broth and carbon source (in some embodiments to 25° C. or less), and thereafter inoculating with the bacteria. In some embodiments, the carbon source is added by first suspending the carbon source in water to form a suspended carbon source and filter sterilizing the suspended carbon source with a 0.2 micrometer cellulose filter.

The provision of the liquid calcification medium can be in any suitable vessel, whether adapted for batch or continuous process. In some embodiments, the $CO_2$ is introduced by agitating the liquid calcification medium, thus exposing it to $CO_2$ in the general environment or general atmosphere. In some embodiments, the $CO_2$ is bubbled through the liquid calcification medium.

In some embodiments, to facilitate the microbially induced precipitation of calcium carbonate, the liquid calcification medium is maintained at a suitable temperature for growth of the bacteria. In some embodiments, the liquid calcification medium is maintained with suitable aeration for growth of the bacteria. In some embodiments, the temperature of the liquid calcification medium is maintained at from 10° C. or more to 42° C. or less and in yet other embodiments the temperature of the liquid calcification medium is maintained at from 25° C. or more to 37° C. or less.

The PCCs are separated from the liquid media via filtration, including membrane filtration or tangential flow filtration.

Reductions to practice have demonstrated that the calcium salt chemistry influences the type of calcite polymorph that is formed. On calcium acetate, lactate, and propionate, the unstable polymorph vaterite was the dominant form of $CaCO_3$. On succinate, a combination of vaterite and calcite was produced, while on pyruvate, calcite was the dominant mineral. The metabolism of the carboxylic acids will influence the metabolic products produced, which in turn sorb to the surface of the mineral and influence the type of polymorph produced. This may also allow tailoring of the final precipitate chemistry.

Per the forgoing, $CO_2$ can be sequestered and PCCs created in the various sizes and shapes. Particulate (µm scale) calcium carbonate has a number of industrial uses: in paper, carbonates are used as a filler and coating, which can increase the smoothness, brightness and help preserve paper; in thermoplastics, carbonates are used as a filler to reduce polymer volume (and cost), modulate elasticity to increase impact resistance, while their thermal conductivity accelerates product manufacturing; in sealants and adhesives, carbonates serves as a filler, thixotropic agent, and reduce shrinkage and sag as polymers set; in coatings (paints), carbonates can serve as an extender and rheology agent, and play an important role in opacity, brightness, gloss and durability; powders are also important in a number of sports, where they reduce hand sweat, such as climbing and gymnastics. Over 130,000 kilotons of carbonate were produced worldwide in 2019 using energy mining extraction technologies. Current industrial PCC production also requires sintering of limestone rock to create lime (CaO). This CaO is then slaked with water and $CO_2$, a process which contributes up to 2% of global $CO_2$ emissions annually (the $CO_2$ liberated from sintering has been calculated at 0.62 tons $CO_2$ per ton PCCs). The invention described herein is the first green alternative for PCC production, with net-negative $CO_2$ release during production.

In light of the foregoing, it should be appreciated that the present invention significantly advances the art in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Past investigators have used environmental bacterial isolates to suggest that microorganisms bring about calcification by simply increasing the pH of media containing excess $Ca^{2+}$ and dissolved $HCO_3^-$. Nonetheless, there are no good model organisms to extensively understand the metabolic principles behind calcification or to manipulate the process for industrial application. Demonstrated below is an *Escherichia coli* (*E. coli*) system based on the metabolism of calcium acetate and calcium succinate that allows the metabolic limitation to be overcome that have previously prevented a deeper understanding of metabolic calcification.

Through the use of *E. coli*, it can be shown that the use of calcium acetate and calcium succinate as carbon sources increases the cellular demand for dissolved $CO_2$ in the media. Through these metabolic processes, the consumption of $HCO_3^-$ and the rising production of $CO_3^{2-}$ ions, an increase in the pH of the medium leads to additional precipitation of $CO_2$-derived carbonates as environmentally stable calcite. By tailoring *E. coli* calcification using different calcium salt chemistries (calcium acetate, calcium succinate, calcium pyruvate, calcium propionate and calcium lactate), the system can be tuned to produce a number of calcite polymorphs and particulates, for use in a number of industrial processes from paper production, adhesives, food preparation, and pharmaceutical production. The system can also be enhanced by engineering an inducible carbonic anhydrase into a gene over-expression system, allowing for increased calcification and $CO_2$ fixation in *E. coli*. It is demonstrated that by using calcium succinate as a $Ca^{2+}$ source, the system can be scaled up to allow significant $CO_2$ fixation as an environmentally stable carbonate.

Calcification by *Escherichia coli*.

Traditionally, researchers have used Boquet B4 media (which contains calcium acetate) to screen environmental isolates for the calcification phenotype. While *E. coli* has not been shown to precipitate $CaCO_3$ using this assay, it does precipitate $CaCO_3$ via ureolysis and in the presence of metastable calcium phosphate, suggesting that calcification is functionally possible. It has previously been demonstrated that *E. coli* in liquid B4 media produces a number of carboxylic and other organic acids, which are produced through a combination of glucose metabolic overflow, acetogenesis, and mixed acid fermentation. As $CaCO_3$ precipitation is related to the pH and saturation index, it was considered that the inability of *E. coli* to calcify on B4 was due to acidification of the media due to the presence of these organic acids. To test this, cultures were set up in B4, with (B4) and without (B4m) the addition of glucose. After one week of growth, no calcification was seen for *E. coli* on B4 (containing glucose), while in the absence of glucose (B4m), calcification was observed. By calibrating cresol red as a pH indicator, it was demonstrated that the media surrounding the *E. coli* colonies had dropped below a pH of 5.0 in the presence of glucose but increased to pH of greater than 8.8 in its absence, demonstrating that calcification can proceed in *E. coli* without the addition of this sugar.

Environmental work has shown that organic acids produced by *E. coli* react with $CaCO_3$ to produce various calcium salts (with acetate as a representative acid in the following reaction):

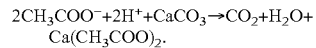

$$2CH_3COO^- + 2H^+ + CaCO_3 \rightarrow CO_2 + H_2O + Ca(CH_3COO)_2.$$

Given the ability to detect these salts in the environment, *E. coli* growth was tested on other calcium salts (calcium propionate, calcium lactate, calcium pyruvate, and calcium succinate) as a mechanism to similarly drive calcification in *E. coli*. As *E. coli* only expresses the citrate transporter under anaerobic conditions, calcium citrate was used to differentiate active calcium metabolism from passive pH effects on calcification in culture. The results demonstrate that when *E. coli* is grown on B4 media with calcium acetate replaced by other calcium salts, there is a distinct pattern of calcification: no calcification was observed when glucose was present but occurred readily on all the provided calcium salts in the absence of glucose. Cresol red indicated that in all cases, the presence of glucose led to acidification of the surrounding media, while in its absence the media became alkali. The exception to this was calcium citrate; *E. coli* grew on the media and produced alkali conditions in the absence of glucose, but the lack of calcification demonstrates the need for a metabolizable calcium salt in promoting calcification.

The amount of calcification observed in the colonies varied depending on both pH and the calcium salt added, although this observation was only qualitative; to date there have been no methods that have allowed quantification of calcification on bacterial colonies. To overcome this limitation and allow a direct comparison of pH versus calcite, a machine learning approach was used to train image analysis software to identify and measure calcite crystal production. The TWS plugin image feature recognition algorithm was used to identify carbonate crystals using a set of colony training images, followed by manually designating areas as crystal, colony, or background. The plugin analyzed subsequent images using this training set and calculated a probability map showing coverage of colonies by calcite crystals. Once the calcite was identified and segmented, percent coverage was calculated using the Analyze Particles function built into ImageJ, making it possible to quantify and compare coverage of calcification in single colonies of *E. coli*. Using this approach, calcification on calcium pyruvate, succinate, lactate, acetate, and propionate was quantified. The data indicated that calcification was more pronounced when calcium acetate and succinate were used for growth: about 46% coverage, compared to about 30% coverage for calcium propionate, calcium lactate, and calcium pyruvate ($p<0.05$ in a Student's T-test). Beyond calcification levels, there did not appear to be any differences between colony count, size, or growth rate between the various media. There was no direct correlation between pH and total calcification, confirming the hypothesis that calcification is not entirely pH dependent and metabolism and the type of calcium salt each play an important role.

The role of acetate as a driver of calcification has been well described: the glyoxylic acid bypass for acetate utilization requires higher $CO_2$ uptake by the cell to synthesize fatty acids in the absence of $CO_2$ produced by the reduction of isocitrate and a-ketoglutarate. This increased utilization of $CO_2$ presumably pulls dissolved $HCO_3^-$ out of the surrounding media, increasing the pH and the saturation index for calcification. Succinate utilization in *E. coli* occurs from the reduction of succinate to fumarate, allowing succinate to directly feed into the citric acid cycle, similarly bypassing needed $CO_2$ produced from the full cycle; this bypass does not occur in metabolism of the weaker calcium salts: pyruvate, lactate, and propionate. To provide a more quantifiable estimation of the role of pH and saturation index in calcification, a liquid culture assay was developed. Liquid cultures were grown and monitored for microbial growth (via an increase in opacity at $OD_{600}$) and insoluble $Ca^{2+}$ ion concentrations as a proxy for calcification. This assay allowed for observation of the onset of calcification with pH changes and indicated that the amount of calcification depended on the calcium source, with the highest amount of calcification occurring with calcium succinate (about 42 ppm $Ca^{2+}$). The amount of calcification was increased with calcium acetate, but not to the same extent (17 ppm $Ca^{2+}$). The data indicated that the calcium salts that induce the highest calcification also demonstrate a rapid pH rise and the onset of calcification (at about 7 hours), although again pH alone was not diagnostic of the onset of calcification. By engineering the *E. coli* carbonic anhydrase gene into an inducible, overexpression plasmid vector, the liquid growth system was used to demonstrate that calcification could be dramatically increased in *E. coli* in a controllable manner.

To confirm that the insoluble $Ca^{2+}$ ions in the media were present in a stable, mineral form XRD was used. To do this, rather than acidifying the captured, insoluble particulates in the media for ICP-MS, they were collected, dried, and subjected to XRD. The results demonstrated that the calcium salt chemistry influenced the type of calcite polymorph that was formed. On calcium acetate, lactate and propionate, the unstable polymorph vaterite was the dominant form of $CaCO_3$. On succinate, a combination of vaterite and calcite was produced, while on pyruvate, calcite was the dominant mineral. The data confirmed that the supplied calcium salt is converted to a mineral form, but that the metabolism of the salt used can influence the type of mineral produced and may allow tailoring of the final precipitate chemistry.

Methods

Growth Conditions and Bacterial Strains

Unless otherwise noted, all chemicals and growth media were obtained from Fisher Scientific (Pittsburg, PA). Calcification was assayed on either solid (with 15 g/L agar) or in liquid calcification B4 media (4 g yeast extract, 10 g glucose), but amended with a variety of different calcium salts [calcium acetate, calcium propionate, calcium L-lactate hydrate, calcium succinate monohydrate, calcium pyruvate, and calcium citrate tribasic tetrahydrate). The basal calcification media was resuspended in 800 mL water, adjusted to pH 7.2 and autoclaved, cooled to 50° C., before 2.5 g of the calcium salt (in 200 mL filter sterilized $dH_2O$). As calcium citrate and calcium succinate are insoluble in water, they were dissolved in 200 mL 0.1 M HCl and readjusted to pH 7.2 before filtering. The minimal B4 media (B4m) was made as described, but without the addition of glucose. When required, cresol red (8 mg/L) was added as a pH indicator (indicator range pH 6.2-8.8).

*E. coli* K-12 type strain MG1655 ($F^-$ lambda$^-$ ΔilvG rfb-50 rph-1) was used to assay calcification phenotypes and grown at 37° C. on LB agar or B4 and amended B4 media plates. A Thermo Fisher Scientific (Waltham, MA, USA) Orion Micro pH 12Ga. needle tipped electrode combined with a Reed (Wilmington, NC, USA) SD-230 pH meter was used to confirm the pH of the agar calibrated using Fisher Scientific (Waltham, Mass., USA) pH 7 and 10 buffers. Unless indicated, all assays were carried out in triplicate. An Olympus (Tokyo, Japan) SZX7 stereomicroscope fitted with an Olympus DFPL I.5× objective and Olympus SCI80 color digital camera was used to Image the single colonies of *E. coli*. Olympus cellSens Standard 2.3 software was used to acquire images with a resolution of 2456×1842 at a standard aspect ratio. For accurate color reproduction the high-quality color image style option was selected and the compartment for insertion of contrast cartridges was left clear.

Quantification of Calcification: Solid Media

As calcification occurred very quickly in colonies at 37° C., *E. coli* MGI655 was grown at room temperature (21° C.) to examine calcification rates. After one week, a minimum of ten individual colonies were chosen at random and imaged using an Olympus SZX7 microscope equipped with an Olympus SCI80 camera. Images were captured using cellSens Standard 2 software (Olympus) and analyzed using the ImageJ plugins Trainable Weka Segmentation (TWS; v3.2.33) and MorphoLibJ (v1.4.1) to measure calcification. The TWS plugin image feature recognition algorithm was used to identify carbonate crystals on the colony using a set of training images of colonies from the same plate, followed by manually designating areas as crystal (red), colony (green), or background (purple) to generate an overlay output. The classification was then scored as .model file for use with other images of similar morphology, which was further refined with additional training images of a series. The plugin analyzed subsequent images using this training set and calculated a probability map showing coverage of colonies by calcite crystals.

Once crystals had been identified and segmented, percent coverage was calculated using the Analyze Particles function built into ImageJ. To obtain individual crystal information, a particle analysis was used. The ImageJ TWS Get probability function was used to generate a probability map of a colony. The image was then formatted as an 8-bit image and the threshold values adjusted until the calcite crystals were selected and the analyze particle function was used, and the minimum size of pixel units was used to mitigate artefact errors. A TWS analysis gave an ROJ overlay allowed measurement of the area, and selections were saved as a .csv file. For the best results, multiple classifiers were produced to account for the change in colony thickness and shadow gradient effects as the colonies grew, changed shape, and became increasingly opaque and occupied by crystals over time. The final overlay of crystal coverage generated by the particle analysis was periodically applied back to the original colony image to check the accuracy of the fit of the classifier and then adjusted where necessary. A detailed description along with ImageJ script was then created.

Quantification of Calcification: Liquid Media

For quantification of calcification in liquid media, 50 mL cultures of calcification media were inoculated with 1 mL of an overnight culture of E. coli grown in 4 g/L yeast extract media grown to $OD_{600}$ 0.75. The cultures were grown in a 250 mL side-arm flask (OWK Life Sciences, Millville, N.J.) at 37° C. with shaking (250 rpm) on an Excella E24 incubated shaker (New Brunswick, Eddison, N.J.). Growth was recorded by taking the optical density ($OD_{600}$) every 30 minutes using a OR 2800 spectrophotometer (Hach, Loveland, Colo.). Once the optical density had reached $OD_{600}$ 0.1, 1 mL samples were taken every hour to quantify any solid $CaCO_3$. To do this, the 1 mL samples were filtered onto a 25 mm Isopore 0.2 μm black PC membrane (Millipore, Burlington, Mass.) using a micro-syringe 25 mm filter holder (Millipore) and washed 10 mL 20 mM HEPES buffer (adjusted to pH 8.3). The membrane was then submerged in 10 mL of a 5% nitric acid (TraceMetal grade) for 30 minutes to dissolve any calcite and centrifuged for 10 minutes at 2,739 rcf on a Survall LegendXTR Centrifuge (Thermo Scientific, Waltham, Mass.) to remove any cell debris. The calcium concentrations of the resulting $HNO_3$ acid solution were measured using a 700 Series ICP-OES (Agilent Technologies, Santa Clara Calif.). Wavelength calibrations were completed using 5 ppm Mn calibration solution, with 0, 3, 7 and 10 ppm calcium ion calibration standards prepared from a 10 ppm calcium stock solution (0.1% v/v $HNO_3$; Inorganic Ventures, Christiansburg, Va.). Analysis of calcium concentration (per mL of culture) was then carried out using ICP Expert II software (Agilent Technologies).

XRD Analyses

For XRD analyses of carbonate minerals, 250 μL of overnight cultures of E. coli grown in B4m ($OD_{600}$ 0.8) was inoculated into 25 mL of liquid media in a 250 mL flask (OWK Life Sciences) and grown for one week at room temperature with shaking at 100 rpm on a SKC-6200 orbital platform shaker (ReioTech, Daejeon, Republic of Korea). Any precipitated minerals were collected by vacuum filtration of the culture onto an MF-Millipore 8.0 μm MCE membrane and washed of cell debris with 15 mL of a 20 mM HEPES buffer at pH 8.3. These filters were allowed to dry for 1 hour at room temperature in a glass Petri plates. The surface of the membranes was then scraped using a metal spatula into a 10 mL glass tube and allowed to dry for an additional 24 hours. This material was then subjected to XRD analysis with an Ultima IV X-ray diffractometer (Rigaku, Tokyo, Japan) operated at 40 KV and 35 mA with a Cu K-alpha energy frequency (wavelength of 1.54 Å). Identification of the diffraction profiles was determined using PDXL 2.1 software package (Rigaku).

What is claimed is:

1. A method for sequestering $CO_2$ and creating precipitated calcium carbonates, the method comprising the steps of:
    (a) providing a liquid calcification medium including:
        a nutrient broth including water and yeast extract, and wherein the nutrient broth is devoid of urea,
        a carbon source selected from the group consisting of calcium formate, calcium acetate, calcium propionate, calcium butyrate, calcium succinate, calcium citrate and mixtures thereof, and
        bacteria that naturally express the chaA gene and wherein the bacteria are Escherichia coli;
    (b) introducing $CO_2$ to the liquid calcification medium; and
    (c) allowing microbial induced carbonate precipitation of calcium carbonate in the liquid calcification medium, thereby sequestering at least some of the $CO_2$ introduced in said step of introducing;
    wherein the nutrient broth is devoid of acidifying carbohydrate sources that drive one or more of: metabolic overflow, acetogenesis, and mixed acid fermentation.

2. The method of claim 1, wherein the liquid calcification medium includes from 1 g to 10 g of the yeast extract per 1 L of water; and from 1 g to 50 g of the carbon source per 1 L of water.

3. The method of claim 2, wherein the liquid calcification medium includes from 2 g/L to 7.5 g/L yeast extract, and from 2.5 g/L to 30 g/L of the carbon source.

4. The method of claim 1, wherein the carbon source is calcium succinate.

5. The method of claim 1, wherein said step of providing a liquid calcification medium comprises the steps of:
    adjusting the nutrient broth to a pH of from pH 6 or more to pH 9 or less and sterilizing the nutrient broth, both prior to providing the bacteria.

6. The method of claim 5, wherein, after the step of sterilizing the nutrient broth, the step of providing a liquid calcification medium comprises the steps of:
    cooling the nutrient broth to room temperature and adding the carbon source, both prior to providing the bacteria.

7. The method of claim 6, wherein adding the carbon source includes suspending the carbon source in water to form a suspended carbon source and filter-sterilizing the suspended carbon source.

8. The method of claim 1, wherein said step of introducing $CO_2$ includes agitating the liquid calcification medium to expose it to $CO_2$ within the surrounding atmosphere.

9. The method of claim 1, wherein said step of introducing carbon dioxide includes bubbling $CO_2$ through the liquid calcification medium.

10. The method of claim 1, wherein said step of allowing precipitation of calcium carbonate includes maintaining the liquid calcification medium at a temperature and providing aeration for growth of the bacteria.

11. The method of claim 10, wherein temperature of the liquid calcification medium is maintained at from 10° C. or more to 42° C. or less.

* * * * *